US010464886B2

(12) United States Patent
Kirmess et al.

(10) Patent No.: US 10,464,886 B2
(45) Date of Patent: Nov. 5, 2019

(54) ALPHA-CYANO-4-HYDROXY-3-IODOCINNAMIC ACID AS A MATRIX IN MALDI MASS SPECTROMETRY

(71) Applicant: Board of Trustees of Southern Illinois University, Carbondale, IL (US)

(72) Inventors: Kristopher M Kirmess, Columbia, IL (US); Gary R Kinsel, Carbondale, IL (US); Kyle Newton Plunkett, Carbondale, IL (US)

(73) Assignee: Board of Trustees of Southern Illinois University, Carbondale, IL (US)

( * ) Notice: Subject to any disclaimer, the term of this patent is extended or adjusted under 35 U.S.C. 154(b) by 0 days.

(21) Appl. No.: 16/201,421

(22) Filed: Nov. 27, 2018

(65) Prior Publication Data

US 2019/0161438 A1    May 30, 2019

Related U.S. Application Data

(60) Provisional application No. 62/592,775, filed on Nov. 30, 2017.

(51) Int. Cl.
*C07C 255/41* (2006.01)
*H01J 49/16* (2006.01)
*H01J 49/00* (2006.01)

(52) U.S. Cl.
CPC ........ *C07C 255/41* (2013.01); *H01J 49/0031* (2013.01); *H01J 49/164* (2013.01); *C07C 2601/16* (2017.05)

(58) Field of Classification Search
CPC ............... C07C 255/41; C07C 2601/16; H01J 49/0031; H01J 49/164

USPC ......................................... 250/281, 282, 288
See application file for complete search history.

(56) References Cited

PUBLICATIONS

Ahn, S.H. et al, "Quantitative Reproducibility of Mass Spectra in Matrix-Assisted Laser Desorption Ionization and Unraveling of the Mechanism for Gas-Phase Peptide Ion Formation," J. Mass Spectrom. 2013, 48; pp. 299-305.
Allwood, D.A. et al., "Plasma Modeling of Matrix-Assited UV Laser-Desorption/Ionization (MALDI)," Appl. Surf. Sci. 1997, 110; pp. 616-620.

(Continued)

*Primary Examiner* — Nicole M Ippolito
*Assistant Examiner* — Hanway Chang
(74) *Attorney, Agent, or Firm* — Denise L. Mayfield; Husch Blackwell LLP

(57) ABSTRACT

A heavy-atom derivative of CHCA, a primary matrix molecule for matrix-assisted laser desorption/ionization mass spectrometry (MALDI-MS), is synthesized and purified. This new matrix molecule α-cyano-4-hydroxy-3-iodocinnamic acid (CHICA) is characterized by $^1$H NMR and mass spectrometry. CHICA is shown to increase MALDI-MS yield for the test analytes human angiotensin II and sex pheromone inhibitor as compared to both CHCA and an alternative heavy-atom CHCA derivative matrix. An optimal CHICA matrix concentration is determined to be 4 mg/mL. Analyte ion yield is shown to be comparable for CHICA and CHCA for analyte concentrations below 0.001 mg/mL. For analyte concentrations above this threshold, use of CHICA resulted in higher analyte yield and significantly lower relative standard deviation.

20 Claims, 9 Drawing Sheets

(56) References Cited

PUBLICATIONS

Allwood, D.A. et al, "Ionization Modeling of Matrix Molecules in Ultraviolet Matrix-Assisted Laser Desorption/Ionization," Rapid Commun. Mass Spectrom. 1997, 11; pp. 499-503.

Allwood, D.A. et al, "Quantitative Fluorescence Measurements Performed on typical Matrix Molecules in Matrix-Assisted Laser Desorption/Ionisation," Chem. Phys. 2000, 261; pp. 457-467.

Bae, Y.J. et al, "Expansion Cooling in the Matrix Plume in Under-recognized in MALDI Mass Spectrometry," J. Am. Soc. Mass Spectrom. 2011, 22; pp. 1070-1078.

Bae, Y.J. et al, "Reproducibility of Temperature-Selected Mass Spectra in the Matrix-Assisted Laser Desorption Ionization of Peptides," Anal. Chem. 2012, 84; pp. 7107-7111.

Bae, Y.J. et al, "Degree of Ionization in MALDI of Peptides: Thermal Explanation for the Gas-Phase Ion Formation," J. Am. Soc. Mass Spectrom. 2012, 23; pp. 1326-1335.

Bae, Y.J. et al, "Why Do the Abundances of Ions Generated by MALDI Look Thermally Determined?," J. Am. Soc. Mass Spectrom. 2013, 24; pp. 1807-1815.

Breuker, K. et al, "Transfer Reactions of Matrix-Assisted Laser Desorption/Ioniation Matrix Monomers and Dimers," J. Am. Soc. Mass Spectrom. 1999, 10; pp. 1111-1123.

Chen, X. et al, "Near-Ultraviolet-Induced Matrix-Assisted Laser Desorption/Ionization as a Function of Wavelength," J. Am. Soc. Mass Spectrom. 1998, 9; pp. 885-891.

Dai, Y. et al, "Two-Layer Sample Preparation: A Method for MALDIMS Analysis of Complex Peptide and Protein Mixtures," Anal. Chem. 1999, 71; pp. 1087-1091.

Dreisewerd, K. et al, "Matrix-Assisted Laser Desorption/Ionization with Nitrogen Lasers of Different Pulse Widths," Int. J. Mass Spectrom. Ion Processs 1996, 154; pp. 171-178.

Ehring, H. et al, "Role of Photoionization and Photochemistry in Ionization Processes of Organic Molecules and Relevance for Matrix-Assisted Laser Desorption Ionization Mass Spectrometry," Org. Mass Spectrom. 1992, 27; pp. 472-480.

Ehring, H. et al, "Studies of the MALDI Process by Luminescence Spectroscopy," J. Mass Spectrom. 1995, 30; 1303-1310.

Ehring, H. et al, "Excited State Relaxation Processes of MALDI-Matrices Studied by Luminescence Spectroscopy," Appl. Surf. Sci. 1996, 96; pp. 577-580.

El-Sayed, M.A., "Triplet state: Its Radiative and Nonradiative Properties," Acc. Chem. Res. 1968, 1; pp. 8-16.

Erb, W.J. et al, "A Study of Gas-Phase Cationization in Matrix-Assisted Laser Desorption/Ionization Time-of-Flight Mass Spectrometry," Rapid Comm. Mass Spectrom. 2006, 20; pp. 2165-2169.

Fenner, N.C. et al, "Laser Used for Mass Analysis," Rev. Sci. Instrum. 1966, 37;(8) pp. 1068-1070.

Hensel, R.R. et al, "Electrospray Sample Preparation for Improved Quantitation in Matrix-assisted Laser Desorption/Ionization Time-of-flight Mass Spectrometry," Rapid Comm. Mass Spectrom. 1997, 11; pp. 1785-1793.

Horneffer, V. et al, "Localization of Analyte Molecules in MALDI Preparations by Confocal Laser Scanning Microscopy," Anal. Chem. 2001, 73; pp. 1016-1022.

Hoyer, T. et al, "Ultrafast Photodimerization Dynamics in alphacyano-4-hydroxycinnamic Acid and Sinapinic Acid Crystals," Chem. Phys. Lett. 2007, 443; pp. 107-112.

Hoyer, T. et al, "Competing Ultrafast Photoinduced Quenching Reactions in Cinnamic Acid Peptide Blends," Phys. Chem. Chem. Phys. 2010, 12; pp. 13052-13060.

Jacques, P. et al, "Tuning the Ion Formation Process from Triplet-Triplet Annihilation to Triplet-Mediated Photoionization," Chem. Phys. Lett. 2003, 378; pp. 185-191.

Jaskolla, T.W. et al, "Using Fluorescence Dyes as a Tool for Analyzing the MALDI Process," J. Am. Soc. Mass Spectrom. 2008, 19; pp. 1054-1061.

Jaskolla, T.W. et al, "4-Chloro-alpha-cyanocinnamic Acid is an Advanced, Rationally Designed MALDI Matrix," Proceedings of the National Academy of Sciences 2008, 105 (34), pp. 12200-12205.

Jaskolla, T.W. et al, "Comparison Between Vacuum Sublimed and Conventional Dried Droplet Preparation in MALDI-TOF Mass Spectrometry," J. Am. Soc. Mass Spectrom. 2009, 20, pp. 1104-1114.

Karas, M. et al, "Influence of the Wavelength in High-Irradiance Ultraviolet Laser Desorption—MS of Organic Molecules," Anal. Chem. 1985, 57; pp. 2935-2939.

Karas, M. et al, "Matrix-Assisted Laser Desorption of Non-Volatile Compounds," Int. J. Mass Spectrom. Ion Proc. 1987, 78; pp. 53-68.

Karas, M. et al, "Laser Desorption Ionization of Proteins with Molecular Masses Exceeding 10,000 Daltons," Anal. Chem. 1988, 60; pp. 2299-2301.

Karas, M. et al, "Ionization in Matrix-Assisted Laser Desorption/Ionization: Singly Charged Molecular Ions are the Lucky Survivors," J. Mass Spectrom. 2000, 35; pp. 1-12.

Karas, M., et al, "Ion Formation in MALDI: The Cluster Ionization Mechanism," Chem. Rev. 2003, 103; pp. 427-439.

Karbach, V. et al, "Do Single Matrix Molecules Generate Primary Ions in Ultraviolet Matrix-Assisted Laser Desorption/Ionization," Rapid Commun. Mass Spectrom. 1998, 12; pp. 968-974.

Kasha, M.J., "Collisional Perturbation of Spin-Orbit Coupling and the Mechanisms of Fluorescence Quenching. A Visual Demonstration of the Perturbation," J. Chem. Phys. 1952, 20 (1); pp. 71-74.

Kinsel, G.R. et al, "Profile and Flight Time Analysis of Bovine Insulin Clusters as a Probe of Matrix-assisted Laser Desorption/Ionization Ion Formation Dynamics," J. Mass Spectrom. 1997, 32; pp. 714-722.

Kinsel, G.R. et al, "Investigation of the Dynamics of Matrix-Assisted Laser Desorption/Ionization Ion Formation Using an Electrostatic Analyzer/Time-of-flight Mass Spectrometer," J. Mass Spectrom. 1999, 34; pp. 684-690.

Kinsel, G.R. et al, "Ionization Energy Reductions in Small 2,5-dihydroxybenzoic Acid-Proline Clusters," J. Mass Spectrom. 2002, 37; pp. 1131-1140.

Kinsel, G.R. et al, "Equilibrium Conditions in Laser-desorbed Plumes: Thermodynamic Properties of alpha-cyano-4-hydroxycinnamic Acid and Protonation of Amino Acids," Eur. J. Mass Spectrom. 2006, 12; pp. 359-367.

Kirmess, K.M. et al, "Excited State Dynamics in the Matrix-Assisted Laser Desorption/Ionization Matrix 2,4,6-trihydroxyacetophenone: Evidence for Triplet Pooling Charge Separation Reactions," Rapid Commun. Mass Spectrom. 2014, 28; pp. 2134-2140.

Kirmess, K.M. et al, "MALDI Ionization Mechanisms Investigated by Comparison of Isomers of Dihydroxybenzoic Acid," J Mass Spectrom. 2016, 51; pp. 79-85.

Klicova, L. et al, "Adiabatic Triplet State Tautomerization of p-Hydroxyacetophenone in Aqueous Solution," J. Phys. Chem. A 2012, 116; pp. 2935-2944.

Knochenmuss, R. et al, "Secondary Ion-Molecule Reactions in Matrix-Assisted Laser Desorption/Ionization," J. Mass Spectrom. 2000, 35; pp. 1237-1245.

Knochenmuss, R., "A Quantitative Model of Ultraviolet Matrix-Assisted Laser Desorption and Ionization," J. Mass Spectrom. 2002, 37; pp. 867-877.

Knochenmuss, R., "A Quantitative Model for UV-MALDI Including Analyte Ion Generation," Anal. Chem. 2003, 75; pp. 2199-2207.

Knochenmuss, R., "Ion Formation Mechanisms in UV-MALDI," Anayst 2006, 131; pp. 966-986.

Knochenmuss, R., "A Bipolar Rate Equation Model of MALDI Primary and Secondary Ionization Processes, with Application to Positive/Negative Analyte Ion Ratios and Suppression Effects," Int. J. Mass Spectrom. 2009, 285; pp. 105-113.

Knochenmuss, R. et al, "Molecular Dynamics Simulations of MALDI: Laser Fluence and Pulse Width Dependence of Plume Characteristics and Consequences for Matrix and Analyte Ionization," J. Mass Spectrom. 2010, 45; pp. 333-346.

(56) References Cited

PUBLICATIONS

Knochenmuss, R., "MALDI Mechanisms: Wavelength and Matrix Dependence of the Coupled Photophysical and Chemical Dynamics Model," The Analyst 2014, 139; pp. 147-156.

Knochenmuss, R., "Energetics and Kinetics of Thermal Ionization Models of MALDI," J. Am. Soc. Mass Spectrom. 2014, 25 pp. 1521-1527.

Kochling, H.J. et al, "In Novel Sample Preparation for MALDI," 43rd Annual ASMS Conference on Mass Spectrometry and Allied Topics, Atlanta, GA., Atlanta, GA., 1995; p. 1225.

Lai, Y.-H. et al, "Analysis of Initial Reactions of MALDI Based on Chemical Properties of Matrixes and Excitation Condition," J. Phys. Chem. B 2012, 116; pp. 9635-9643.

Land, C.M. et al, "Investigation of the Mechanism of Intracluster Proton Transfer for Sinapinic Acid to Biomolecular Analytes," Am. Soc. Mass Spectrom. 1998, 9; pp. 1060-1067.

Land, C.M. et al, "The Mechanisms of Matrix to Analyte Proton Transfer in Clusters of 2,5-Dihydroxybenzoic Acid and the Tripeptide VPL," Am. Soc. Mass Spectrom. 2001, 12; pp. 726-731.

Li, L. et al, "Analysis of Single Mammalian Cell Lysates by Mass Spectrometry," J. Am. Chem. Soc. 1996, 118; pp. 11662-11663.

Liang, C.W. et al, "MALDI Mechanism of Dihydroxybenzoic Acid Isomers: Desorption of Neutral Matrix and Analyte," J. Phys. Chem. B 2013, 117; pp. 5058-5064.

Lin, H.-Y. et al, "Fluorescence Spectroscopy of UV-MALDI Matrices and Implications of Ionization Mechanisms," J. Chem. Phys. 2014, 141; pp. 164307-1-164307-11.

Lin, H.-Y.; et al, "Is Energy Pooling Necessary in Ultraviolet Matrix-Assisted Laser Desorption/Ionization?" Rapid Commun. Mass Spectrom. 2014, 28; pp. 77-82.

Liu, B.-L. et al, "Initial Ionization Reaction in Matrix-Assisted Laser Desorption/Ionization," J. Phys. Chem. B 2010, 114; pp. 10853-10859.

Ludemann, H.C. et al, "Annihilation in Ultraviolet Matrix-Assisted Laser Desorption/Ionization Studied by Fluorescence Spectroscopy,". Rapid Commun. Mass Spectrom. 2002, 16; pp. 1287-1294.

Niu, S. et al, "Direct Comparison of Infrared and Ultraviolet Wavelngth Matrix-Assisted Laser Desoprtion/Ionization Mass Spectrometry of Proteins," J. Am. Soc. Mass Spectrom. 1998, 9; pp. 1-7.

Petrone, D.A. et al, "Harnessing Reversible Oxidative Addition: Application of Diionated Aromatic Compounds in the Carboiodination Process," Angew. Chem. Int. Ed. 2013, 52; pp. 10635-10638.

Pillman, H.A. et al, "Effects of Ethanol on the Organization of Phosphocholine Lipid Bilayers," J. Phys. Chem. B 2010, 114; pp. 3840-3846.

Preston-Schaffter, L.M. et al, "Effects of Heavy-Atom Substituents on Matrices Used for Matrix-Assisted Laser Desorption-Ionization Mass Spectrometry," Am. Soc. Mass Spectrom. 1994, 5; pp. 800-806.

Price, D.M. et al, "Sublimation Properties of x,y-Dihydroxybenzoic Acid Isomers as Model Matrix Assisted Laser Desorption Ionisation (MALDI) Matrices," Thermochim. Acta 1999, 327; pp. 167-171.

Przybilla, L. et al, "Mass Spectrometry of Insoluble Giant Polycyclic Aromatic Hydrocarbons by a New Method of Sample Preparation," Anal. Chem. 2000, 72; pp. 4591-4597.

Purdy, B.B. et al, "Changes in the Photophysical Properties with Heavy Atoms and the Effects of Modulus for 4-Phenylphenol in Solid-Matrix Luminescence," Appl. Spectrosc. 1992, 46; pp. 988-993.

Qiao, H. et al, "Analyte Distributions in MALDI Samples Using MALDI Imaging Mass Spectrometry," Int. J. Mass Spectrom. 2009, 281; pp. 41-51.

Sadeghi, M. et al, "Crystallite Size Dependence of Volatilization in Matrix-Assisted Laser Desorption Ionization," Appl. Surf. Sci. 1998, 127/129; pp. 226-234.

Setz, P.D. et al, "Exciton Mobility and Trapping in a MALDI Matrix," J. Phys. Chem. A 2005, 109; pp. 4030-4037.

Su, C. et al, "Coherent Vibrational Motion during the Excited-State Intramolecular Proton Transfer Reaction in o-hydroxyacetophenone," J. Phys. Chem. A 2002, 106; pp. 11997-12001.

Tanaka, K. et al, "Protein and Polymer Analyses up to m/z 100,000 by Laser Ionization Time-of-Flight Mass Spectrometry," Rapid Commun. Mass Spectrom. 1988, 2; (8) pp. 151-153.

Tisdale, E.J. et al, "Total Synthesis of seco-lateriflorone," Tetrahedron 2003, 59; pp. 6873-6887.

Vorm, O. et al, "Improved Resolution and Very High Sensitivity in MALDI TOF of Matrix Surfaces Made by Fast Evaporation," Anal. Chem. 1994, 66; pp. 3281-3287.

Williams, T.I. et al, "Effect of Matrix Crystal Structure on Ion Abundance of Carbohydrates by Matrix-Assisted Laser Desorption/Ionization Fourier Transform Ion Cyclotron Resonance Mass Spectrometry," Rapid Comm. Mass Spectrom. 2007, 21; pp. 807-811.

Xiang, F. et al, "Growing Protein-doped Sinapic Acid Crystals for Laser Desorption: an Alternative Preparation Method for Difficult Samples," Organic Mass Spectrometry 1993, 28; pp. 1424-1429.

Xiang, F. et al, "A Method to Increase Contaminant Tolerance in Protein Matrix-Assisted Laser Desorption/Ionization by the Fabrication of Thin Protein-Doped Polycrystalline Films," Rapid Comm. Mass Spectrom. 1994, 8; pp. 199-204.

Yassin, F.H. et al, "Computational Estimates of the Gas-Phase Basicities, Proton Affinities and Ionization Potentials of the Six Isomers of Dihydroxybenzoic Acid," Mol. Phys. 2005, 103; (2-3) pp. 183-189.

Vastola, F.J. et al, "Ionization of Organic Salts by Laser Ionization," Adv. Mass Spectrom. 1968, 4; 107-111.

Gross, J.H., "Matrix-Assisted Laser Desorption/Ionization, Mass Spectrometry," Springer: Verlag Berlin Heidelberg, 2004.

Birks, J.B., "Photophysics of Aromatic Molecules," Wiley Interscience: New York, 1970.

Birks, J.B., "Organic Molecular Photophysics," Wiley: New York, 1973.

"Catalog Handbook of Fine Chemicals," St. Louis, 2012.

Yassin, F. "Computational Studies of MALDI Matrices," University of Texas Arlington, 2004.

Turro, N.J., "Modern Molecular Photochemistry," University Science Books: Sausalito, CA, 1991.

Ingle, J.D. et al, "Spectrochemical Analysis," Prentice Hall: Englewood Cliffs, NJ, 1988.

Jaskolla, T.W. et al, "4-Chloro-α-Cyanocinnamic Acid is an Advanced, Rationally Designed MALDI Matrix," PNAS, vol. 105, No. 34, Aug. 26, 2008, pp. 12200-12205.

Price, D.M. et al, "Sublimation Properties of x,y-dihydroxybenzoic Acid Isomers as Model Matrix Assisted Laser Desorption Ionisation (MALDI) Matrices," Thermochimica Acta, vol. 327, 1999, pp. 167-171.

ALPHA-CYANO-4-HYDROXY-3-IODOCINNAMIC ACID AS A MATRIX IN MALDI MASS SPECTROMETRY

CROSS-REFERENCE TO RELATED APPLICATION

This application claims priority of U.S. Provisional Application Ser. No. 62/592,775, filed Nov. 30, 2017, whose disclosures are incorporated herein by reference.

BACKGROUND OF THE INVENTION

The present invention relates to use of α-cyano-4-hydroxycinnamic acid derivatives as a matrix in MALDI mass spectrometry of analytes.

Mass spectrometry (MS) is a common analytical technique used to sort ionized molecules in a sample by their mass-to-charge ratio. A challenge within the field of MS is that ionization can damage molecules within a sample, with organic molecules and biomolecules being particularly susceptible. The matrix-assisted laser desorption/ionization (MALDI) technique was developed in the 1980's as a way to ionize biomolecules and large organic molecules with reduced molecule fragmentation. The technique involves mixing the molecules of interest (analyte) with a matrix material and irradiating the combined sample with a laser; this irradiation releases charges from the matrix that ionize the analyte.

MALDI relies on the selection of a proper organic matrix molecule. Several criteria must be met in order for an organic molecule to be a useful MALDI matrix. Because most UV-MALDI mass spectrometers incorporate a pulsed laser, commonly either a nitrogen (337 nm) or frequency tripled Nd:YAG laser (355 nm), the matrix must contain a chromophore which allows for sufficient absorption at the chosen wavelength. This absorption is essential for electronic excitation of the molecule to occur. Secondly, the matrix must be weakly acidic, as this allows for the donation of a proton from the matrix to the analyte. While some matrices exhibit several acidic protons, it is commonly the most acidic proton in the excited or ion state which is transferred to the analyte during ionization. Another important consideration when determining a suitable matrix is the ability of the matrix to co-crystallize with the analyte. This co-crystallization between matrix and analyte is essential as it brings the analyte into the gas-phase upon desorption. Subsequently, the matrix helps create gas-phase ions of the analyte with minimal fragmentation. Typical analytes that are suitable for MALDI-MS include biomolecules (e.g., oligonucleotides such as DNA and RNA, proteins, peptides, sugars, lipids, medical substances, plant metabolites, etc.) and large organic molecules (e.g., polymers, dendrimers, catenanes, rotaxanes, and other macromolecules).

The analysis begins by mixing a large molar excess of the matrix with the analyte. The ratio of matrix to analyte, typically 500:1 to 5000:1, is often varied to achieve optimal signal-to-noise ratio. Various deposition methods for both the matrix and analyte have been thoroughly investigated, including the dried droplet, fast evaporation, and slow crystallization approaches. These methods all encompass a few crucial steps in the sample preparation. First, a drop of matrix solution, typically 1 µL, is placed onto the stainless steel MALDI target and allowed to dry. 1 µL of the analyte solution is then placed onto the dried matrix spot and is also allowed to air dry. Upon drying of the analyte solution, co-crystallization of the two compounds can occur to form inhomogeneous matrix-analyte crystals. These inhomogeneous crystals are then irradiated by the pulsed laser which results in desorption and ionization of the matrix and analyte. A dense plume of desorbed matrix and analyte is formed, from which ions are accelerated down the flight tube of the MS to be detected individually.

Common MALDI matrices include 2,3-dihydroxybenzoic acid (2,3-DHB), 2,4-dihydroxybenzoic acid (2,4-DHB), 2,5-dihydroxybenzoic acid (2,5-DHB), 2,6-dihydroxybenzoic acid (2,6-DHB), 3,4-dihydroxybenzoic acid (3,4-DHB), 3,5-dihydroxybenzoic acid (3,5-DHB), α-cyano-4-hydroxycinnamic acid (CHCA), ferulic acid (FA), and sinapic acid (SA), 2,4,6-trihydroxyacetophenone.

Although commonly referred to as the "gold standard" MALDI-MS matrix, MS performed using CHCA matrices commonly suffer from lack of signal reproducibility. Specifically, the analyte ion signals supported by CHCA lack the sensitivity required to effectively analyze many analytes.

Here, it was found that the introduction of heavy atoms (e.g., halogens such as fluoro, chloro, bromo, or iodo substitution) to the aromatic ring of CHCA, while retaining the 4-OH group, overcomes these disadvantages. In particular, the addition of halogens (i.e., F, Cl, Br, or I) to the aromatic ring of CHCA has drastically improved analyte ionization, ion signal reproducibility (demonstrated from relative standard deviation), and interferences from low-mass ions, relative to the non-substituted matrix.

BRIEF SUMMARY OF THE INVENTION

The present invention provides matrix compounds of the general formula I

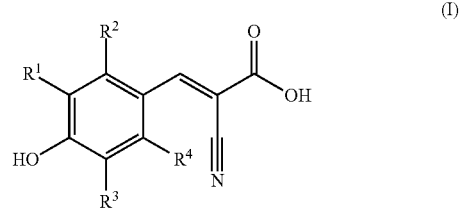

(I)

wherein
$R^1$ is H, F, Cl, Br, or I;
$R^2$ is H, F, Cl, Br, or I;
$R^3$ is H, F, Cl, Br, or I;
$R^4$ is H, F, Cl, Br, or I;
and wherein at least one of $R^1$, $R^2$, $R^3$, and $R^4$ is F, Cl, Br, or I.

In another embodiment, the matrix compound is the molecule α-cyano-4-hydroxy-3-iodocinnamic acid (CHICA), which contains an iodo-group substitution. CHICA is also referred to herein as a compound comprising Formula (II):

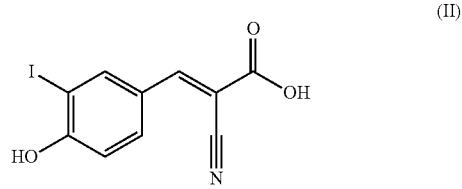 [SMILES: N#C/C(=C\c1ccc(O)c(I)c1)C(=O)O]

(II)

In yet another embodiment, a method for performing MALDI-MS is disclosed. The method for performing MALDI-MS includes:

obtaining a matrix compound of the general formula:

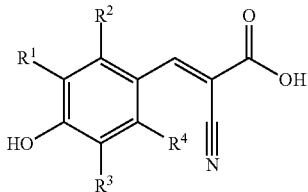

wherein
R$^1$ is selected from H, F, Cl, Br, or I;
R$^2$ is selected from H, F, Cl, Br, or I;
R$^3$ is selected from H, F, Cl, Br, or I;
R$^4$ is selected from H, F, Cl, Br, or I;
wherein at least one of R$^1$, R$^2$, R$^3$, and R$^4$ is selected from F, Cl, Br, or I;
dissolving the matrix compound in a water-miscible solution to form a matrix solution;
applying the matrix solution and an analyte to a MALDI plate;
allowing the MALDI plate to dry; and
performing MALDI-MS on the MALDI plate.

In yet another embodiment, a method for synthesizing an α-cyano-4-hydroxy-3-iodocinnamic acid matrix material is disclosed. This method includes:
(a) performing a condensation using a cyanoacetic acid, a 4-hydroxy-3-iodobenaldehyde, and a catalyst, where the cyanoacetic acid, the 4-hydroxy-3-iodobenaldehyde, and the ammonium acetate catalyst are mixed and refluxed in a solvent that is at least partially miscible in water and where water formed as a result of the condensation reaction is removed;
(b) cooling the reaction mixture to a temperature between −10° C. and 60° C.; and
(c) isolating a solid crude product from the reaction mixture.

Use of CHICA as a MALDI-MS matrix results in significantly higher analyte measurement sensitivity as compared to identical MALDI-MS analyses performed with CHCA matrices. Specifically, standard deviations of analyte peak areas are reduced for MALDI-MS analyses performed with CHICA matrices as compared to CHCA matrices. This reduction in standard deviation is advantageous due to the high level of reproducibility often desired for MALDI-MS analyses.

DETAILED DESCRIPTION OF THE INVENTION

Figure 1:
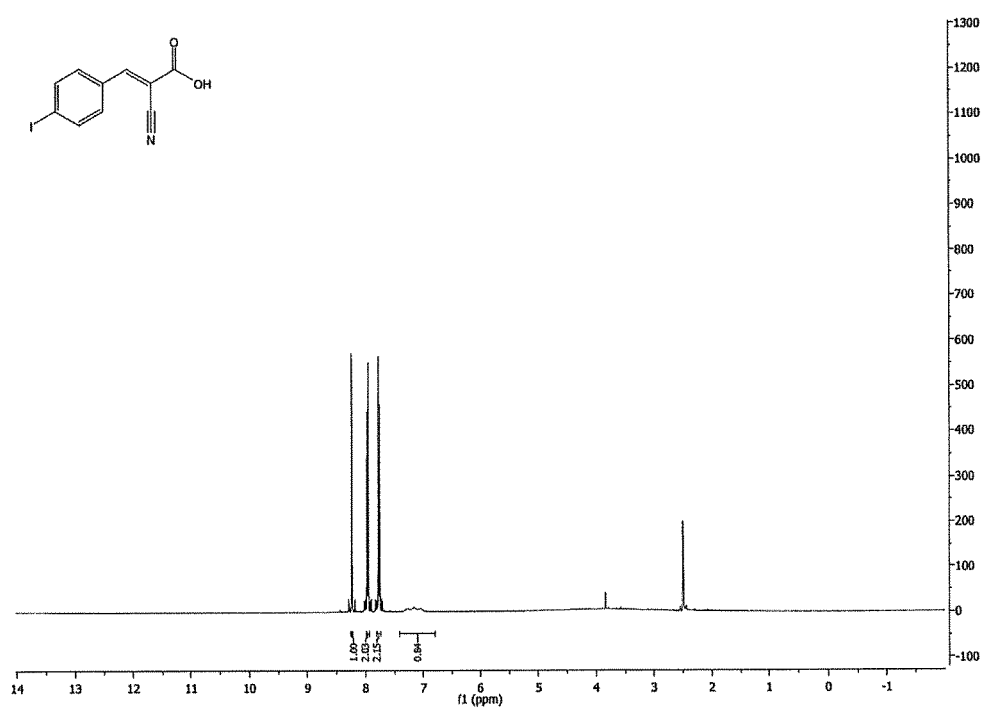
FIG. 1 shows $^1$H NMR spectrum of purified α-cyano-4-iodocinnamic acid.

The present invention provides matrix compounds of the general formula I

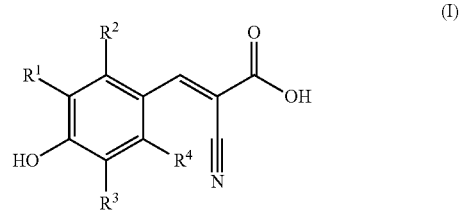

(I)

Wherein
R$^1$ is H, F, Cl, Br, or I;
R$^2$ is H, F, Cl, Br, or I;
R$^3$ is H, F, Cl, Br, or I;
R$^4$ is H, F, Cl, Br, or I;
and wherein at least one of R$^1$, R$^2$, R$^3$, and R$^4$ is F, Cl, Br, or I.

Alternatively, R$^1$ is selected from F, Cl, Br, or I, while each of R$^2$, R$^3$, and R$^4$ is H. In another embodiment, R$^1$ is F, while each of R$^2$, R$^3$, and R$^4$ is H. In another embodiment, R$^1$ is Cl, while each of R$^2$, R$^3$, and R$^4$ is H. In another embodiment, R$^1$ is Br, while each of R$^2$, R$^3$, and R$^4$ is H. In another embodiment, R$^1$ is I, while each of R$^2$, R$^3$, and R$^4$ is H. In another embodiment, R$^2$ is selected from F, Cl, Br, or I, while each of R$^1$, R$^3$, and R$^4$ is H. In another embodiment, R$^2$ is F, while each of R$^1$, R$^3$, and R$^4$ is H. In another embodiment, R$^2$ is Cl, while each of R$^1$, R$^3$, and R$^4$ is H. In another embodiment, R$^2$ is Br, while each of R$^1$, R$^3$, and R$^4$ is H. In another embodiment, R$^2$ is I, while each of R$^1$, R$^3$, and R$^4$ is H. In yet another embodiment, the compound is α-cyano-4-hydroxy-3-iodocinnamic acid. Halogen means fluoro, chloro, bromo, or iodo, which can be represented by their respective chemical symbol: F, Cl, Br, or I. Hydrogen is represented herein by its chemical symbol: H.

Furthermore, the compounds of the present are useful in the performance of MALDI-MS. The method for performing MALDI-MS includes:

obtaining a matrix compound of the general formula:

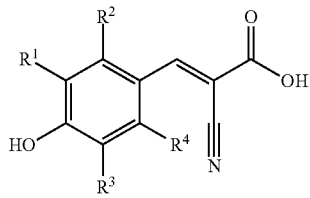

wherein
R¹ is selected from H, F, Cl, Br, or I;
R² is selected from H, F, Cl, Br, or I;
R³ is selected from H, F, Cl, Br, or I;
R⁴ is selected from H, F, Cl, Br, or I;
wherein at least one of R¹, R², R³, and R⁴ is selected from F, Cl, Br, or I;
dissolving the matrix compound in a water-miscible solution to form a matrix solution;
applying the matrix solution and an analyte to a MALDI plate;
allowing the MALDI plate to dry; and
performing MALDI-MS on the MALDI plate.

In one embodiment, the method for performing MALDI-MS includes dissolving the matrix compound in a water-miscible solution to form a matrix solution, applying the matrix solution and an analyte to a MALDI plate, allowing the MALDI plate to dry, and performing MALDI-MS on the MALDI plate. Applying the matrix solution and an analyte to a MALDI plate may include mixing the matrix solution and analyte prior to applying to the MALDI plate, applying the matrix solution to the MALDI plate and allowing the MALDI plate to dry for a first time and then applying the analyte to the MALDI plate and allowing the MALDI plate to dry for a second, or applying the analyte to the MALDI plate and allowing the MALDI plate to dry for a first time and then applying the matrix solution to the MALDI plate and allowing the MALDI plate to dry for a second time. Furthermore, alternating the application and drying of matrix solution and analyte can be repeated several times. In one embodiment of the method for performing MALDI-MS, the matrix is α-cyano-4-hydroxy-3-iodocinnamic acid.

Water-miscible solutions may include, but are not limited to, aqueous and non-aqueous solvents, organic and inorganic salts, buffers, acids, and bases. The matrix solution may have a concentration of about 0.001 to 1000 mg/mL, preferably about 0.01 to 100 mg/mL, most preferably about 0.1 to 10 mg/mL. The matrix and/or analyte may be deposited onto a MALDI plate by any means known in the art, which includes, but not limited to, the dried droplet method, surface preparation method, sublimation method, or spray method. The dried droplet method and surface preparation method is preferred. The MALDI plate may be dried by any suitable method in the art, which includes drying by evaporation at ambient conditions or under reduced pressure.

The molecule α-cyano-4-hydroxy-3-iodocinnamic acid (CHICA), also referred to herein as a compound comprising Formula (II), is synthesized, characterized, and utilized in matrix-assisted laser desorption/ionization (MALDI) mass spectrometry (MS) analyses as described herein.

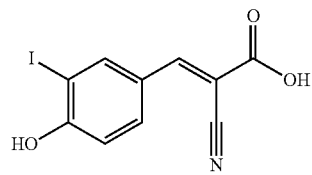

CHICA differs from the CHCA parent molecule by the addition of an iodine located ortho in relation to the hydroxyl group. The addition of a halogen to the base structure of a MALDI matrix is hypothesized to alter its excited-state properties by decreasing the singlet excited state lifetime while theoretically increasing triplet-triplet pooling reactions.

CHICA is synthesized by performing a condensation using cyanoacetic acid and 4-hydroxy-3-iodobenaldehyde precursors in the presence of an acid-base catalyst. Water formed as a result of the condensation reaction is removed and the reaction mixture is cooled to a temperature between −10° C. and 60° C. to yield a solid crude product.

In particular, the synthesis of CHICA includes performing a Knoevenagel condensation using a cyanoacetic acid, a 4-hydroxy-3-iodobenaldehyde, and a suitable acid/base catalyst, such as ammonium acetate. The cyanoacetic acid, 4-hydroxy-3-iodobenaldehyde, and catalyst may be used in a weight proportion of 0.192 to 0.45 to 0.025, respectively. Furthermore, the catalyst may range from 0.01 to 0.5 weight proportion. The cyanoacetic acid, the 4-hydroxy-3-iodobenaldehyde, and catalyst may be mixed and refluxed in a solvent that is at least partially miscible in water and where water formed as a result of the condensation reaction is removed. A suitable solvent includes, but is not limited to, toluene. Alternatively, other suitable methods known in the art can be employed instead of refluxing, such as the use of molecular sieves. Water from the condensation reaction may be removed using methods known in the art, such as the use of a Dean-Stark apparatus. Once the reaction mixture has been refluxed, the reaction mixture may be cooled to a temperature between −10° C. and 60° C. and the crude product may be isolated from the reaction mixture.

The crude product may be purified by column chromatography, such as silica gel flash column chromatography. For silica gel flash column chromatography, mobile phase may be any organic mixture of polar and nonpolar solvents with 0-95% polar solvent and 5-100% nonpolar solvent. Example nonpolar solvents include pentane, hexane, heptane, toluene, benzene, and cyclohexane. Example polar solvents include ethyl acetate, dichloromethane, acetone, methanol, and ethyl ether. Preferably, the mobile phase is 75% hexane and 25% ethyl acetate. The purified product may then be concentrated under vacuum to remove solid product from solvent. The product may be further purified by recrystallization. Any organic solvent with water 5-95% concentration (v/v) may be implemented. Preferably, a solution of 1:1 ratio by volume of methanol and water is used for recrystallization.

Experimental

Materials

The materials, including analytes tested, used to produce the data presented herein include 3-iodo-4-methoxybenzaldehyde (97%), 4-iodobenzaldehyde (96%), boron tribromide (BBr₃) (99.99%), cyanoacetic acid (99%), anhydrous magnesium sulfate (99.5%), ammonium acetate (98%), and α-cyano-4-hydroxycinnamic acid (CHCA; 98%), all purchased from Sigma-Aldrich (St. Louis, Mo.). Also used were anhydrous dichloromethane, ethyl acetate, acetonitrile, and toluene, all purchased from Fisher Scientific (Waltham, Mass.). The human angiotensin II and sex pheromone inhibitor analytes were purchased from Bio-Rad (Hercules, Calif.).

Matrix Purification

The purchased CHCA matrix material was purified before use according to the following protocol: Thin films of the MALDI matrices were created by subliming each matrix onto precleaned 1"×1" aluminum substrates. 100 mg of the respective matrix was placed at the bottom of the sublimation chamber and the substrate was affixed to the bottom of the chamber via vacuum adhesive tabs. After five minutes under reduced pressure, cold water (10° C.) was circulated through a cold finger (configured on the sublimation chamber) and heat was applied by a sand bath at the base of the chamber. The temperature of the sand bath was monitored throughout sublimation and maintained below the melting point of the sample; sample melting points are described in Price et. al., Thermochimica Acta 1999 (327) and in the Catalog Handbook of Fine Chemicals 2012 (St. Louis). After 20 minutes, the heat source was removed from the chamber, which remained under vacuum for an additional ten minutes. The chamber was then vented to atmospheric pressure. The sublimed matrix films appeared to be visually uniform but were not characterized further. Excess sublimed matrix was scraped from the bottom of the cold finger and used.

MALDI-MS

MALDI mass spectrometry was performed using the following protocol: 4-hydroxy-3-iodobenzaldehyde and α-cyano-4-hydroxy-3-iodocinnamic acid were dissolved in a 2:1 acetonitrile/water solution containing 0.1% TFA with concentrations of 5 mg/mL. 0.5 µL of each solution was spotted to each target on the pre-cleaned 96-target polished steel MALDI plate and allowed to air dry. All mass spectra were acquired using a Bruker Microflex time-of-flight (TOF) mass spectrometer (Bruker Daltonics, Leipzig, Germany). The instrument was operated in positive ion linear mode and using pulsed extraction (18.75 kV acceleration). Laser desorption was performed using a nitrogen laser (337 nm). The ion extraction delay time was set to 100 ns while spectra of 100 laser shots were summed and collected.

Analyte ionization efficiencies of the matrices were determined using human angiotensin II and sex pheromone inhibitor as test analytes in MALDI-MS studies. Analyte concentrations were varied from $5.00\times10^{-1}$ to $1.00\times10^{-4}$ mg/mL. Tested matrices and analytes were dissolved in a 2:1 solution of acetonitrile/water containing 0.1% TFA. Matrix and samples were spotted onto the MALDI target as described above.

Matrix and Sample Spotting

Purified MALDI matrices were dissolved in an acetonitrile/water mixture (2:1 v/v) containing 0.1% TFA to yield final concentrations of 10 mg/mL. Human angiotensin II and PEG were also dissolved in the same acetonitrile/water mixture. The concentration of both human angiotensin II and PEG were 1.00×10-4 mg/mL. To the pre-cleaned 96 spot polished steel MALDI plate, 0.5 µL of each matrix solution was spotted and allowed to air dry. Once dry, 0.5 µL of the peptide/polymer solution was spotted onto each dried matrix spot and allowed to air dry for 30 minutes before analysis by MALDI-MS. All mass spectra were acquired using a Bruker Microflex LR time-of-flight (TOF) mass spectrometer (Bruker Daltonics, Billerica, Mass.). The instrument was operated in positive ion linear mode and using pulsed extraction (18.75 kV acceleration). Laser desorption was performed using a nitrogen laser (337 nm). The ion extraction delay time was set to 100 ns while spectra of 100 laser shots were summed and recorded for each matrix.

UV-Vis Spectroscopy

UV-Vis spectra were collected by dissolving the matrices in a 2:1 (v/v) solution of acetonitrile/water with final concentrations of 5 mg/mL. Ten microliters of each solution were then spotted on the inside of a quartz cuvette and allowed to dry. The dried films appeared to be uniform across the entire surface of the cuvette. The cuvettes containing the dried matrix were then placed in a Cary 100 spectrometer and absorption spectra were collected from 200-500 nm.

Synthesis of α-Cyano-4-Iodocinnamic Acid

Figure 2:
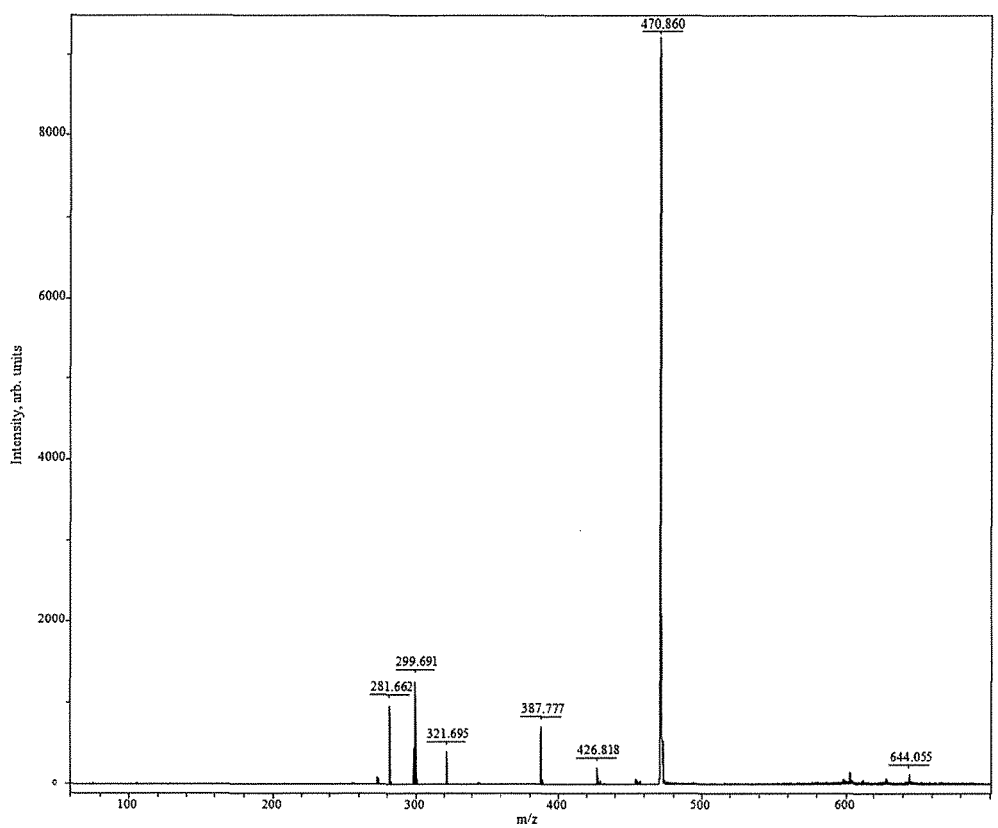
FIG. 2 shows laser desorption/ionization of purified α-cyano-4-iodocinnamic acid.

Alpha-cyano-4-iodocinnamic acid was synthesized as previously described by Jaskolla et al. *PNAS* 2008 (105:34) using a standard Knoevenagel condensation. Briefly, 1.5 g of 4-iodobenzaldehyde, 0.61 g of cyanoacetic acid, and 0.083 g of ammonium acetate were placed in a round-bottom flask with 15 mL of toluene and allowed to reflux with constant stirring. Water which formed as a result of the condensation reaction was continuously removed throughout the experiment using a Dean-Stark apparatus and fresh toluene was added to the reaction. After three hours, the solution was cooled to 50° C. and filtered. The crude solid was then washed with copious amounts of deionized water and collected. Purification of the crude product was performed by recrystallization in 1:1 methanol/water. The final yield of purified product was 48%. FIG. 1 and FIG. 2 show the respective proton NMR spectrum and MALDI MS of the synthesized α-cyano-4-iodocinnamic acid. $^1$H NMR (400 MHz, DMSO) δ 8.24 (s, 1H), 7.96 (d, J=8.4 Hz, 2H), 7.77 (d, J=8.6 Hz, 2H), 7.16 (s, 1H). MALDI MS)(M$^{+\cdot}$) m/z 299.691.

Other embodiments may use other condensation techniques or reactions. Some embodiments may use different ratios of solvents, precursors, and/or catalysts.

Synthesis of 4-Hydroxy-3-Iodobenzaldehyde

Figure 3:
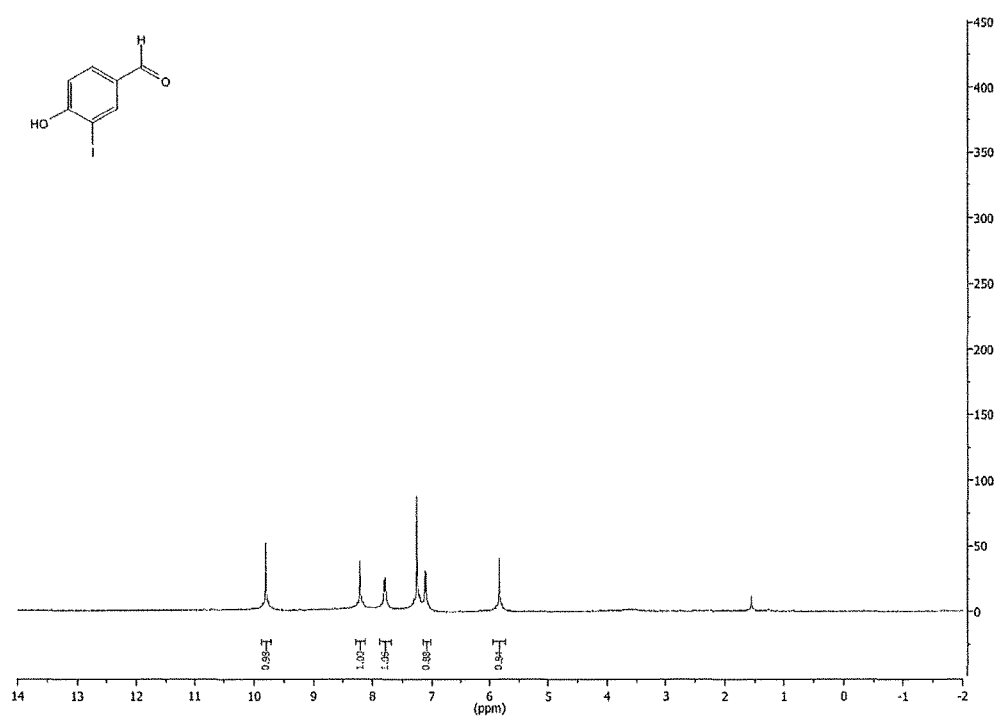
FIG. 3 shows $^1$H NMR spectrum of purified 4-hydroxy-3-iodobenzaldehyde.
Figure 4:
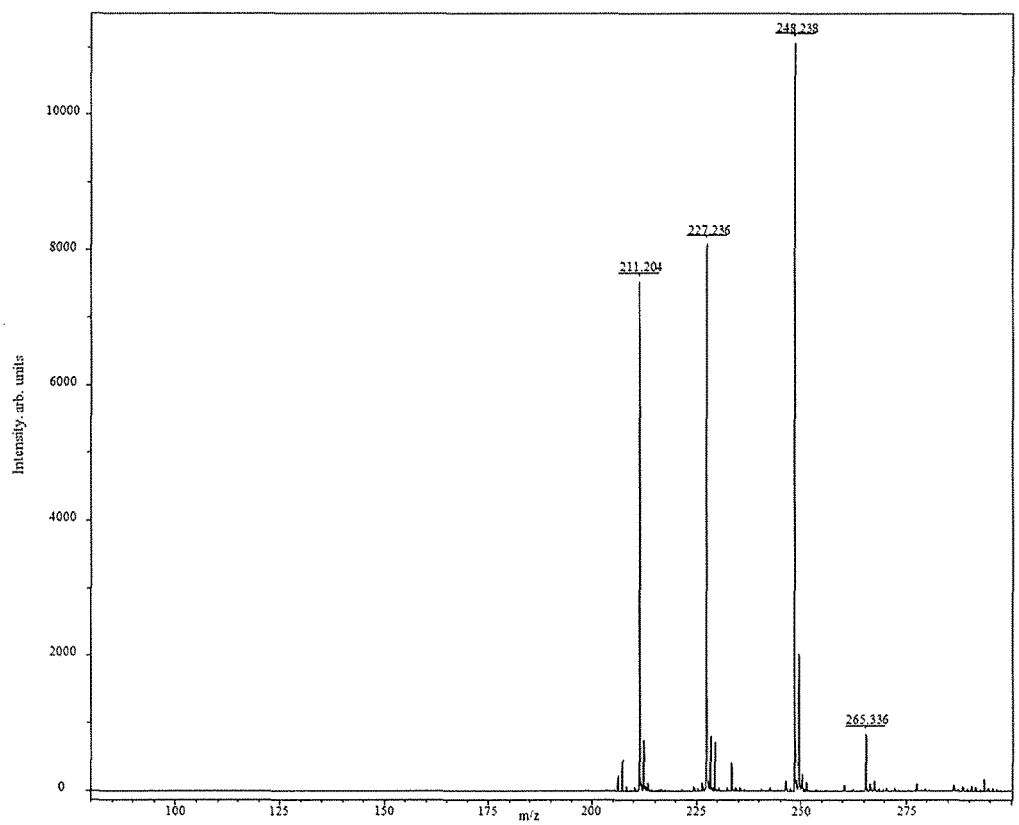
FIG. 4 shows MALDI mass spectrum of purified 4-hydroxy-3-iodobenzaldehyde.

The compound 4-hydroxy-3-iodobenzaldehyde, used as the precursor benzaldehyde for synthesis of CHICA, was synthesized from 3-iodo-4-methoxybenzaldehyde as described by Petrone et. al., Angew. Chem. Int. Ed. 2013 (52). Approximately 1 g of 3-iodo-4-methoxybenzaldehyde was added to 100 mL of anhydrous dichloromethane and stirred at 0° C. 0.405 mL of boron tribromide was added dropwise to the solution and was allowed to warm to room temperature over a period of 24 hours. Approximately 40 mL of water was then added to the solution to quench the reaction. The aqueous and organic layers were then separated and the aqueous layer was extracted with two 100 mL washings of ethyl acetate. The ethyl acetate layers were collected and combined with the organic layer from the initial separation. The combined organic layer was washed with 100 mL of water and 100 mL of brine and was then dried over anhydrous magnesium sulfate, filtered, and concentrated under vacuum. Thin layer chromatography was then applied to the crude product to determine the conditions for optimal separation by silica gel flash column chromatography. A mobile phase composition of 80% hexanes and 20% ethyl acetate provided the best separation of product from starting material. Fractions collected from the column which contained the product compound were combined and concentrated under vacuum. The final yield of purified product was approximately 46%. FIG. 3 and FIG. 4 show the respective proton NMR spectrum and MALDI MS of the synthesized 4-hydroxy-3-iodobenzaldehyde. $^1$H NMR (400 MHz, CDCl$_3$) δ 9.81 (s, 1H), 8.22 (s, 1H), 7.80 (d, J=6.8 Hz, 1H), 7.12 (d, J=8.3 Hz, 1H), 5.84 (s, 1H). MALDI MS (M+H$^+$) m/z 248.238.

Synthesis of α-Cyano-4-Hydroxy-3-Iodocinnamic Acid (CHICA)

Synthesis of α-cyano-4-hydroxy-3-iodocinnamic acid, the iodine-substituted CHCA termed CHICA herein, is similar to that previously described by Jaskolla et al. *PNAS* 2008 (105:34). A key difference, however, is that the benzaldehyde precursor used for CHICA synthesis incorporated the hydroxyl functional group.

A Knoevenagel condensation was performed using cyanoacetic acid and 4-hydroxy-3-iodobenaldehyde, using ammonium acetate as the catalyst. In other embodiments, non-Knoevenagel condensations may be used. Some embodiments may use an alternative acid-base catalyst.

Briefly, 0.45 g of 4-hydroxy-3-iodobenaldehyde, 0.183 g of cyanoacetic acid, and 0.025 g of ammonium acetate were stirred and refluxed in 25 mL of toluene. During this reaction, a water separator was used to remove water which formed as a result of the condensation reaction. Other embodiments may employ different proportions of 4-hydroxy-3-iodobenaldehyde, cyanoacetic acid, and/or catalyst. For the precursor amounts described herein, a viable range of ammonium acetate catalyst is 0.01 g to 0.5 g. Some embodiments may use, in lieu of toluene, another solvent that is miscible or partially miscible in water. Further embodiments may forego reflux techniques in lieu of molecular sieves.

After three hours, the reaction mixture was cooled to 50° C., filtered to yield a crude product, and washed with copious amounts of deionized water. In other embodiments, the reaction mixture may be cooled to a temperature between –10° C. and 60° C. or cooling may occur after an amount of time different from three hours has elapsed. Some embodiments may isolate the solid crude product via decanting or other methods. Further embodiments may omit the step of washing the crude product with deionized water or may use a different solvent to wash the crude product.

Silica gel flash column chromatography was performed on the crude product using a mobile phase consisting of 75% hexane and 25% ethyl acetate. Fractions which contained the product compound were combined and concentrated under vacuum. Other embodiments may omit this purification step, use only recrystallization to purify the crude product, or use generic column chromatography for purification. In some embodiments the mobile phase solution is an organic mixture of polar and nonpolar solvents with 0-95% polar solvent and 5-100% nonpolar solvent. Example nonpolar solvents include pentane, hexane, heptane, toluene, benzene, and cyclohexane. Example polar solvents include ethyl acetate, dichloromethane, acetone, methanol, and ethyl ether.

Further purification of the product was performed by recrystallization in an 1:1 methanol:water solution. Other embodiments may omit this purification step, perform purification prior to column chromatography, perform recrystallization in a solution containing between 5% and 95% of any organic solvent mixed with between 95% and 5% water, or purify the product via a method other than recrystallization.

Figure 5:
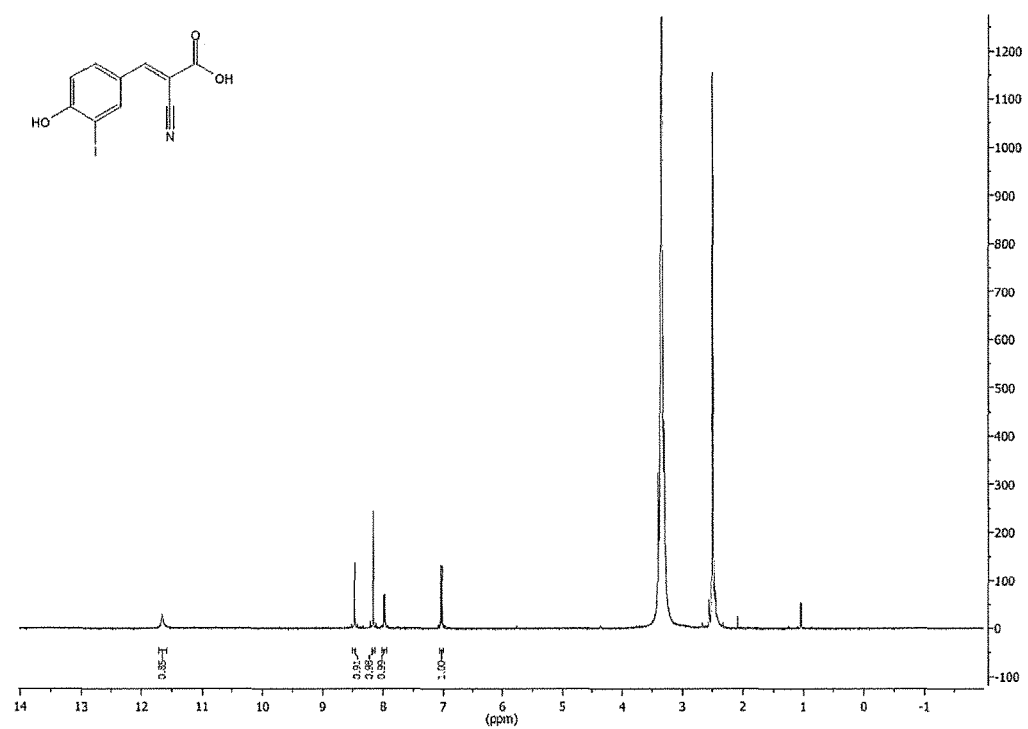
FIG. 5 shows $^1$H NMR spectrum of purified α-cyano-4-hydroxy-3-iodocinnamic acid.
Figure 6:
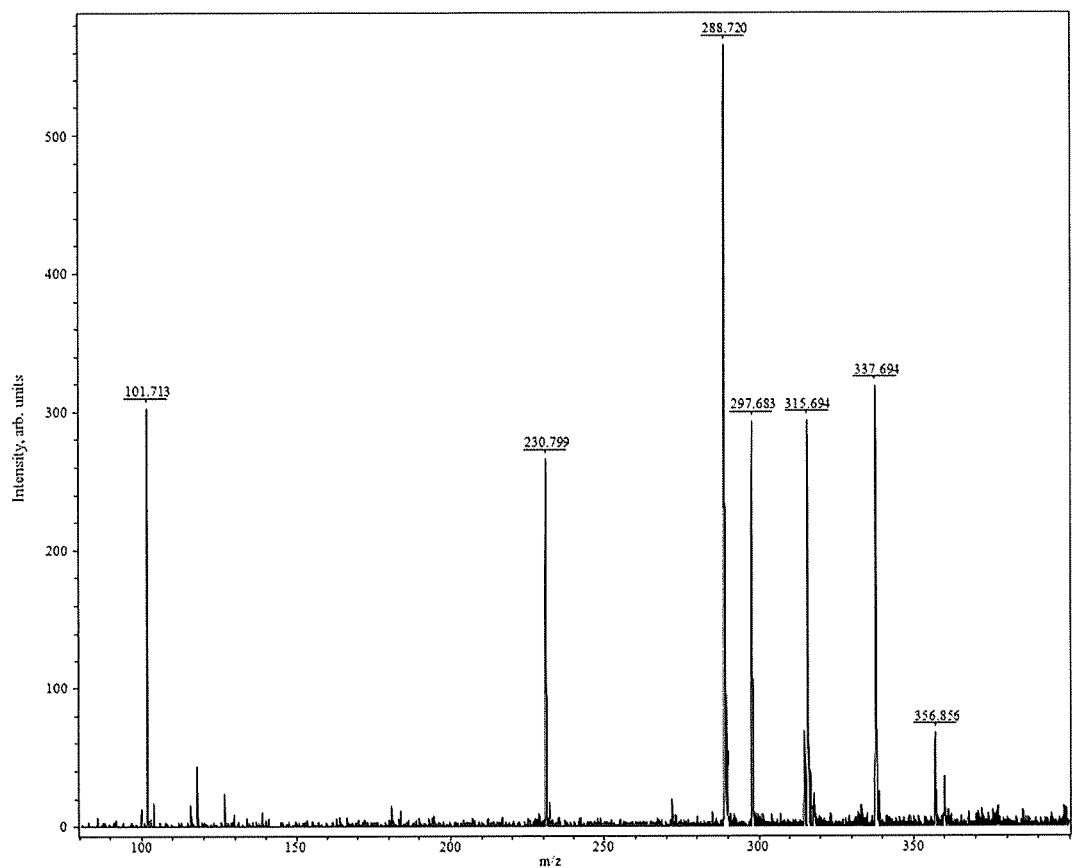
FIG. 6 shows laser desorption/ionization mass spectrum of purified α-cyano-4-hydroxy-3-iodocinnamic acid.

Final yield of the iodo-substituted CHCA derivative, CHICA, was approximately 60%. FIG. 5 and FIG. 6 show the respective proton NMR spectrum and MALDI MS of the synthesized CHICA. $^1$H NMR (400 MHz, DMSO) δ 11.65 (s, 1H), 8.47 (d, J=2.2 Hz, 1H), 8.16 (s, 1H), 7.98 (dd, J=8.5, 2.2 Hz, 1H), 7.03 (d, J=8.5 Hz, 1H). MALDI MS (M$^{+\cdot}$) m/z 315.694.

CHICA Results and Performance

The CHICA matrix described herein produced unexpectedly good results when used as a matrix for MALDI-MS. The prior art teaches away from inclusion of a heavy atom such as iodine in MALDI-MS matrices. Specifically, Jaskolla et al. suggest in *PNAS* 2008 (105:34) that 4-chloro-α-cyanocinnamic acid is a superior matrix in comparison to all other heavy-atom substituted matrices, including 4-iodo-α-cyanocinnamic acid. For both the chloro- and iodo-substituted derivatives of CHCA investigated by Jaskolla et al. for the purpose of producing an improved matrix, the hydroxyl group was replaced by a halogen of interest. Notably, the molecules synthesized by Jaskolla et. al. were designed without a hydroxyl group. The hydroxyl group typically contains the most acidic proton of CHCA-like molecules in the gas phase, and Jaskolla et al. believed that decreasing the proton affinity of the redesigned matrices resulted in enhanced ion yield in the MALDI mass spectrum. In contrast to this perspective, the results presented herein show excellent performance of a CHCA-like molecule that includes both a heavy atom (iodine) and a hydroxyl group. In fact, the gas-phase properties of the matrices do not appear to be important in the primary ionization mechanism within MALDI.

Comparison Between α-Cyano-4-Iodocinnamic Acid and CHICA

Figure 7:
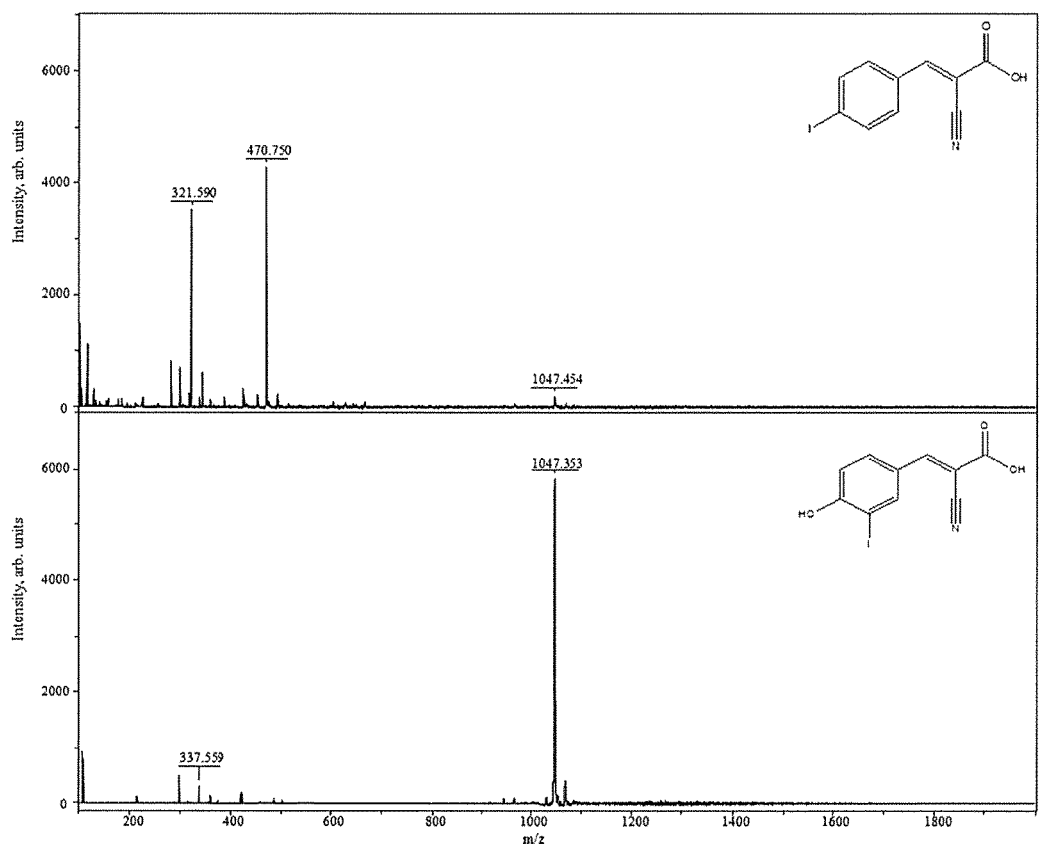
FIG. 7 shows mass spectra of the analyte human angiotensin II while using α-cyano-4-iodocinnamic acid (top) and α-cyano-4-hydroxy-3-iodocinnamic acid (bottom) as matrices. Each mass spectra is averaged of 100 laser shots.

The matrix proposed by Jaskolla, α-cyano-4-iodocinnamic acid, and CHICA were synthesized and their performance as a MALDI matrix investigated using MALDI MS. The two synthesized matrices were compared side by side for their ability to protonate an analyte of interest (FIG. 7). The mass spectrum using α-cyano-4-iodocinnamic acid as the matrix (top) shows the base peak at m/z 470.750 which represents [2M–I]$^{+\cdot}$. The second most intense peak at m/z 321.590 results from [M+Na]$^+$. The peak located at m/z 1047.454 represents the weak signal associated with the protonated analyte.

Several factors could be responsible for the weak analyte ion signal. The absence of the hydroxyl group could decrease the ability of the matrix to donate a proton, resulting in a limited analyte ion signal. Another potential reason for decreased analyte ionization is the formation of matrix clusters within the expanding MALDI plume. Evidence for this phenomenon is observed in FIG. 7 at m/z 470.750. The formation of a photoionized dimer occurs through the apparent loss of an iodine atom. The formation of a trimer can also be seen near m/z 643.577, however it is in low abundance and the formation of a dimer seems to be more energetically favored.

The mass spectrum located on the bottom of FIG. 7 was collected using CHICA as the matrix. Here, the base peak is located at m/z 1047.353 which is representative of the protonated analyte; the signal located at m/z 337.559 is that of [M+Na]$^+$. Proton transfer from the matrix to the analyte appears to be more efficient than the previously synthesized α-cyano-4-iodocinnamic acid. The analyte ion signal obtained from using CHICA is more than ten times greater than from using α-cyano-4-iodocinnamic acid. No evidence of cluster formation is observed in the mass spectrum featuring a CHICA matrix. It is theorized that the formation of a dimer is hindered due to the presence of the hydroxyl group on the matrix. While the creation of clusters may have certain advantages, here, we believe it negatively affects the gas-phase acidity of the molecule, making the molecule less likely to donate a proton to the analyte of interest.

The mass spectrum obtained using a CHICA matrix is also relatively "clean," featuring high signal-to-noise ratios. Although minimal fragmentation of the analyte was observed for spectra taken using either matrix, the use of α-cyano-4-iodocinnamic acid resulted in the formation of several low-mass ions. These ions in the low mass region have the potential to be problematic if structural studies on the analyte are to be performed. Studies such as peptide sequencing would become more challenging while using the matrix α-cyano-4-iodocinnamic acid. The embodiment of the present invention, CHICA, resulted in significantly less formation of low-mass ions. Subsequent studies focus on comparisons of α-cyano-4-hydroxy-3-iodocinnamic acid and compare its performance to the gold standard matrix, CHCA.

Determination of Matrix Concentration for Optimum Analyte Ion Signal

The experiments detailed herein demonstrate the superiority of the iodo-substituted matrix in comparison to CHCA. In the first set of experiments, the optimum matrix concentrations for maximizing analyte ion signal were identified by varying concentrations of the two matrices as the concentration of the analyte (human angiotensin II) was held constant. It is proposed that the matrix concentration for maximizing analyte ion signal is a solution of about 0.001 to 1000 mg/mL, preferably about 0.01 to 100 mg/mL, most preferably about 0.1 to 10 mg/mL.

Figure 8:
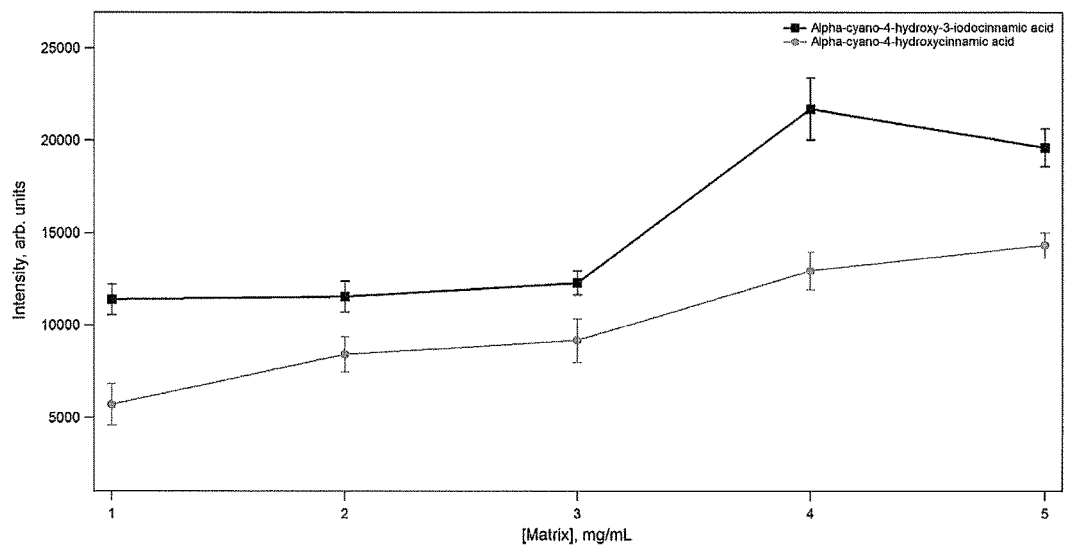
FIG. 8 shows averaged signal intensity for human angiotensin II at varying matrix concentrations. The concentration of the analyte was held constant at 0.01 mg/mL. Each data point represents an averaged signal from 100 laser shots.

As seen in FIG. 8, CHICA yielded a more intense analyte ion signal throughout the entire range of matrix concentrations. This is particularly intriguing because there are nearly twice as many (lower mass) CHCA matrix molecules than there are (higher mass) CHICA molecules at the same concentration (mg/mL). The percentage relative standard deviation (% RSD) for CHICA ranged from 5-8%, with an average % RSD of 6.58%. CHCA resulted in % RSD which ranged from 5-20%, with an average of 11.4%. These results suggest that CHICA produces a more reproducible signal than CHCA at this analyte concentration. The most intense ion signal for the iodo-substituted CHICA matrix resulted from a concentration of 4 mg/mL, whereas the most intense ion signal for the CHCA matrix resulted from using a 5 mg/mL solution. With this observation, we conclude that proton transfer occurs more efficiently in CHICA as compared to CHCA.

CHICA Absorption Spectra

Figure 9:
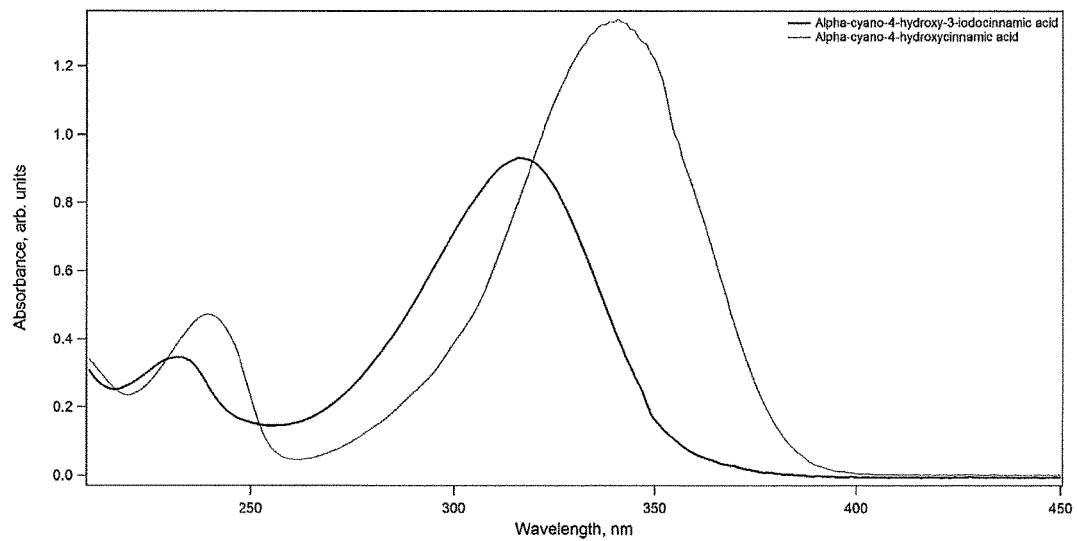
FIG. 9 shows solid state absorption spectra of α-cyano-4-hydroxy-3-iodocinnamic acid and α-cyano-4-hydroxycinnamic acid.

Solid-state absorption spectra for both CHICA and CHCA are shown in FIG. 9. Increased absorptivity for CHCA versus CHICA is observed for both the $S_1$ and $S_2$ bands. At 337 nm (the wavelength used for laser desorption in all MALDI-MS analysis presented herein), CHCA featured a three-fold increase in absorbance as compared to the iodo-substituted CHICA matrix. It thus appears that, at least for CHICA and CHCA matrices, absorption of the laser irradiation is not directly correlated to analyte ion formation. FIG. 9 also shows hypsochromic shift for the iodo-substituted CHICA matrix in comparison to CHCA. Shifts of 25 nm and 7 nm were observed for the $S_1$ and $S_2$ bands, respectively, with both the high and low energy tails of the bands affected. These shifts support the hypothesis that addition of the iodine affected the molecular characteristics of the molecule.

Analyte Ionization Efficiency for CHICA and CHCA

MALDI mass spectra were collected using each of the two matrices, with the peptides human angiotensin II and sex pheromone inhibitor serving as the analytes of interest. Concentrations of the matrices were held constant at 4 mg/mL for CHICA and 5 mg/mL for CHCA for all analyses that follow. Analyte concentrations were varied from $5.00 \times 10^{-1}$ to $1.00 \times 10^{-4}$ mg/mL.

Figure 10:
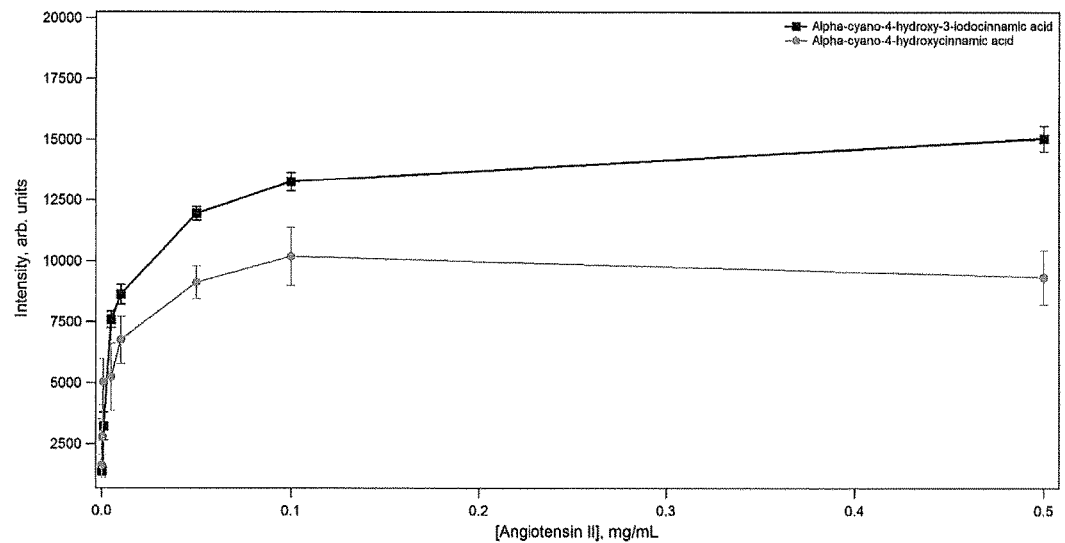
FIG. 10 shows averaged signal intensity for human angiotensin II at 4 mg/mL α-cyano-4-hydroxy-3-iodocinnamic acid and 5 mg/mL CHCA. Each data point represents an averaged signal from 100 laser shots.

Identical logarithmic trends for the human angiotensin II analyte ion signal were observed for spectra taken with CHICA versus CHCA matrices (FIG. 10). Both matrices exhibited strong signal for analyte concentrations from $5.00 \times 10^{-1}$ to $1.00 \times 10^{-3}$ mg/mL. Signal intensity was generally higher for CHICA throughout the concentration range. However, the analyte signal was nearly identical for both matrices at analyte concentrations below $1.00 \times 10^{-3}$ mg/mL. The ion signal reproducibility was drastically improved using CHICA, relative to CHCA. The % RSD of human angiotensin II using CHICA ranged from 2-18%, with an average % RSD of 6.32%. Similarly, CHCA produced % RSD for human angiotensin II ranging from 7-32%, with an average % RSD of 18.4%.

Figure 11:
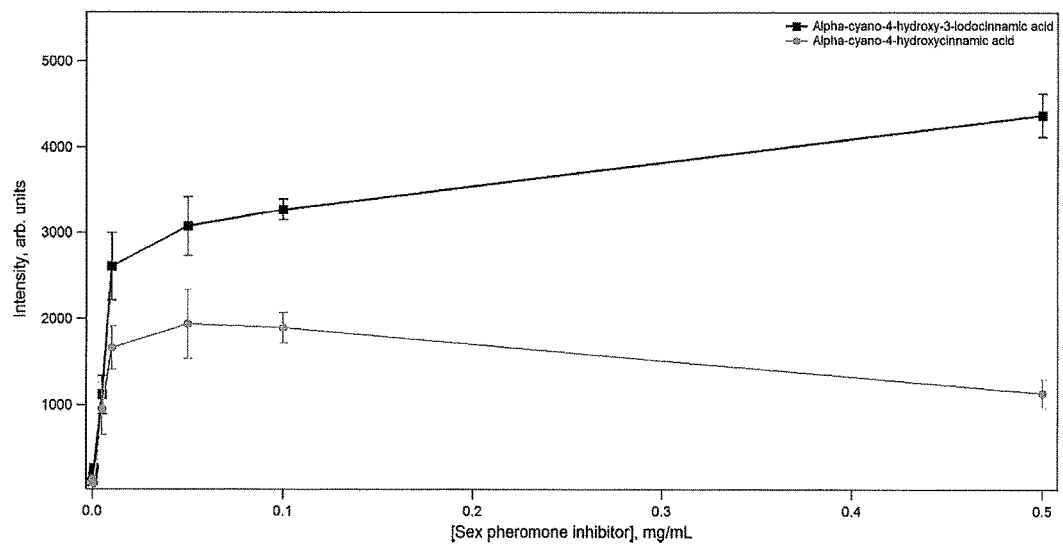
FIG. 11 shows averaged signal intensity for sex pheromone inhibitor at 4 mg/mL α-cyano-4-hydroxy-3-iodocinnamic acid and 5 mg/mL CHCA. Each data point represents an averaged signal from 100 laser shots.

The ion signal reproducibility for sex pheromone inhibitor was drastically improved using CHICA, relative to CHCA. The % RSD for sex pheromone inhibitor while using CHICA as the matrix ranged from 3-26%, with an average % RSD of 13.7%. The % RSD while using CHCA as the matrix ranged from 9-34%, with an average % RSD of 22.6% (FIG. 11).

The CHICA was then compared with CHCA to determine which matrix yielded a more intense analyte ion yield. While maintaining a constant analyte concentration, it was found that CHICA resulted in more analyte ion yield for all matrix concentrations tested. From this experiment, the optimal matrix concentration was determined. The peak concentration for CHICA was found to be 4 mg/mL, which CHCA resulted in an optimal concentration of 5 mg/mL. These optimal concentrations were then used as the concentration of human angiotensin II was varied. At low analyte concentrations (0.001 mg/mL), CHICA and CHCA are comparable in analyte ion yield. At analyte concentrations 0.001 mg/mL and higher, CHICA resulted in an increased analyte ion yield over CHCA. Additionally, the ion signal reproducibility was drastically improved using CHICA, relative to CHCA. The % RSD was lower for CHICA than for CHCA. Similar results were obtained while using sex pheromone inhibitor as the test analyte.

The invention claimed is:
1. A compound of Formula I:

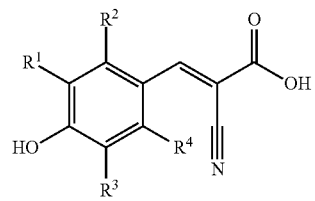

wherein
  $R^1$ is selected from H, F, Cl, Br, or I;
  $R^2$ is selected from H, F, Cl, Br, or I;
  $R^3$ is selected from H, F, Cl, Br, or I;

$R^4$ is selected from H, F, Cl, Br, or I;
and wherein at least one of $R^1$, $R^2$, $R^3$, and $R^4$ is selected from F, Cl, Br, or I.

2. The compound according to claim 1, wherein $R^1$ is selected from F, Cl, Br, or I; and each of $R^2$, $R^3$, and $R^4$ is H.

3. The compound according to claim 1, wherein $R^1$ is F; and each of $R^2$, $R^3$, and $R^4$ is H.

4. The compound according to claim 1, wherein $R^1$ is Cl; and each of $R^2$, $R^3$, and $R^4$ is H.

5. The compound according to claim 1, wherein $R^1$ is Br; and each of $R^2$, $R^3$, and $R^4$ is H.

6. The compound according to claim 1, wherein $R^1$ is I; and each of $R^2$, $R^3$, and $R^4$ is H.

7. The compound according to claim 1, wherein $R^2$ is selected from F, Cl, Br, or I; and each of $R^1$, $R^3$, and $R^4$ is H.

8. The compound according to claim 1, wherein $R^2$ is F; and each of $R^1$, $R^3$, and $R^4$ is H.

9. The compound according to claim 1, wherein $R^2$ is Cl; and each of $R^1$, $R^3$, and $R^4$ is H.

10. The compound according to claim 1, wherein $R^2$ is Br; and each of $R^1$, $R^3$, and $R^4$ is H.

11. The compound according to claim 1, wherein $R^2$ is I; and each of $R^1$, $R^3$, and $R^4$ is H.

12. The compound according to claim 1, wherein the compound is α-cyano-4-hydroxy-3-iodocinnamic acid.

13. A method for performing MALDI-MS, said comprising:
obtaining a matrix compound of the general formula:

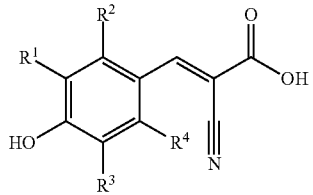

wherein
$R^1$ is selected from H, F, Cl, Br, or I;
$R^2$ is selected from H, F, Cl, Br, or I;
$R^3$ is selected from H, F, Cl, Br, or I;
$R^4$ is selected from H, F, Cl, Br, or I;
wherein at least one of $R^1$, $R^2$, $R^3$, and $R^4$ is selected from F, Cl, Br, or I;
dissolving the matrix compound in a water-miscible solution to form a matrix solution;
applying the matrix solution and an analyte to a MALDI plate;
allowing the MALDI plate to dry; and
performing MALDI-MS on the MALDI plate.

14. The method of claim 13, wherein applying the matrix solution and an analyte to a MALDI plate comprises mixing the matrix solution and analyte prior to applying to the MALDI plate.

15. The method of claim 13, wherein applying the matrix solution and an analyte to a MALDI plate comprises applying the matrix solution to the MALDI plate and allowing the MALDI plate to dry for a first time and then applying the analyte to the MALDI plate and allowing the MALDI plate to dry for a second time.

16. The method of claim 13, wherein applying the matrix solution and an analyte to a MALDI plate comprises applying the analyte to the MALDI plate and allowing the MALDI plate to dry for a first time and then applying the matrix solution to the MALDI plate and allowing the MALDI plate to dry for a second time.

17. The method of claim 13, wherein the matrix compound is α-cyano-4-hydroxy-3-iodocinnamic acid.

18. A method for synthesizing an α-cyano-4-hydroxy-3-iodocinnamic acid matrix material comprising:
(a) performing a condensation using a cyanoacetic acid, a 4-hydroxy-3-iodobenaldehyde, and a catalyst, where the cyanoacetic acid, the 4-hydroxy-3-iodobenaldehyde, and the ammonium acetate catalyst are mixed and refluxed in a solvent that is at least partially miscible in water and where water formed as a result of the condensation reaction is removed;
(b) cooling the reaction mixture to a temperature between −10° C. and 60° C.; and
(c) isolating a solid crude product from the reaction mixture.

19. The method of claim 18, further comprising the step of purifying the crude product by column chromatography.

20. The method of claim 18, further comprising the step of further purifying the crude product by recrystallization.

* * * * *